US011510613B2

(12) United States Patent
Iida et al.

(10) Patent No.: US 11,510,613 B2
(45) Date of Patent: Nov. 29, 2022

(54) BIOLOGICAL CONDITION DETERMINING APPARATUS AND BIOLOGICAL CONDITION DETERMINING METHOD

(71) Applicants: MINEBEA MITSUMI Inc., Nagano (JP); NATIONAL UNIVERSITY CORPORATION CHIBA UNIVERSITY, Chiba (JP)

(72) Inventors: Norihito Iida, Sagamihara (JP); Shiroh Isono, Chiba (JP)

(73) Assignees: MINEBEA MITSUMI Inc., Nagano (JP); NATIONAL UNIVERSITY CORPORATION CHIBA UNIVERSITY, Chiba (JP)

(*) Notice: Subject to any disclaimer, the term of this patent is extended or adjusted under 35 U.S.C. 154(b) by 168 days.

(21) Appl. No.: 15/881,027

(22) Filed: Jan. 26, 2018

(65) Prior Publication Data

US 2018/0146917 A1 May 31, 2018

Related U.S. Application Data

(63) Continuation of application No. PCT/JP2016/072323, filed on Jul. 29, 2016.

(30) Foreign Application Priority Data

Jul. 30, 2015 (JP) .............................. JP2015-151309

(51) Int. Cl.
*A61B 5/00* (2006.01)
*A61B 5/08* (2006.01)
(Continued)

(52) U.S. Cl.
CPC ............. *A61B 5/4818* (2013.01); *A61B 5/00* (2013.01); *A61B 5/08* (2013.01); *A61B 5/0816* (2013.01);
(Continued)

(58) Field of Classification Search
CPC .... A61B 5/4818; A61B 5/1116; A61B 5/6892
See application file for complete search history.

(56) References Cited

U.S. PATENT DOCUMENTS 6,450,957 B1* 9/2002 Yoshimi ................. A61B 5/113
600/309
6,547,743 B2* 4/2003 Brydon ................. A61B 5/0816
600/529
(Continued)

FOREIGN PATENT DOCUMENTS

JP 2003-235813 A 8/2003
JP 2006-263454 A 10/2006
(Continued)

OTHER PUBLICATIONS

Written Opinion for corresponding Singapore Patent Application No. 11201800647S dated Nov. 22, 2018.
(Continued)

*Primary Examiner* — John R Downey
*Assistant Examiner* — Anant A Gupta
(74) *Attorney, Agent, or Firm* — Pearne & Gordon LLP

(57) ABSTRACT

There is provides a biological condition determining apparatus for determining a biological condition of a subject on a bed. A biological condition determining apparatus includes a plurality of load detectors which are placed in the bed or under feet of the bed and which detect a load of the subject, a biological information extracting unit which extracts biological information from an output of at least one of the load detectors, a determining unit which determines the biological condition of the subject by comparing the extracted biological information with a referential information prepared beforehand, and an output unit which outputs the biological condition of the subject determined by the determining unit.

12 Claims, 12 Drawing Sheets

(51) Int. Cl.
  *A61B 5/107* (2006.01)
  *A61B 5/11* (2006.01)
(52) U.S. Cl.
  CPC ............ *A61B 5/107* (2013.01); *A61B 5/1116* (2013.01); *A61B 5/6892* (2013.01)

(56) References Cited

U.S. PATENT DOCUMENTS

| | | | | |
|---|---|---|---|---|
| 6,646,556 | B1* | 11/2003 | Smith | A61B 5/6892 340/666 |
| 8,545,416 | B1* | 10/2013 | Kayyali | A61M 16/0051 600/534 |
| 2005/0107722 | A1* | 5/2005 | Ozaki | A61B 5/6887 600/587 |
| 2008/0275349 | A1* | 11/2008 | Halperin | A61B 5/447 600/484 |
| 2010/0240982 | A1* | 9/2010 | Westbrook | A61B 5/4818 600/538 |
| 2011/0112442 | A1* | 5/2011 | Meger | A61B 5/0002 600/595 |
| 2013/0060150 | A1* | 3/2013 | Song | A61N 1/3627 600/484 |
| 2013/0245502 | A1* | 9/2013 | Lange | A61B 5/1102 600/595 |
| 2014/0005502 | A1* | 1/2014 | Klap | A61B 5/1116 600/300 |
| 2014/0194793 | A1* | 7/2014 | Nakata | G01S 13/87 601/48 |
| 2014/0259417 | A1* | 9/2014 | Nunn | A61F 5/56 5/614 |
| 2015/0196766 | A1* | 7/2015 | Rosenberg | A61B 5/4836 607/42 |
| 2020/0064182 | A1* | 2/2020 | Lin | A61B 5/6894 |

FOREIGN PATENT DOCUMENTS

| | | |
|---|---|---|
| JP | 4002905 B2 | 11/2007 |
| JP | 2008-049023 A | 3/2008 |
| JP | 2008-264338 A | 11/2008 |
| JP | 2009-072214 A | 4/2009 |
| JP | 2010-148700 A | 7/2010 |
| JP | 4829020 B2 | 11/2011 |
| JP | 2014-180432 A | 9/2014 |
| JP | 2014-210137 A | 11/2014 |
| WO | 2011/009085 A2 | 1/2011 |

OTHER PUBLICATIONS

Written Opinion for corresponding International Application No. PCT/JP2016/07323 dated Sep. 13, 2016 and English translation.
International Preliminary Report on Patentability for corresponding International Application No. PCT/JP2016/07323 dated Jan. 30, 2018.
Notice of Reasons for Refusal dated Feb. 5, 2019 for corresponding Japanese Application No. 2015-151309 and partial English translation.
Extended European Search Report dated Feb. 5, 2019 for corresponding European Application No. 16830607.4.
International Search Report for corresponding International Application No. PCT/JP2016/07323 dated Sep. 13, 2016.
Notice of Reasons for Rejection dated Nov. 19, 2019 for corresponding Japanese Application No. 2015-151309 and English translation.
Chinese Office Action dated May 6, 2020 for corresponding Chinese Application No. 201680044004.7 and computer-generated English translation.
Decision of Refusal dated Mar. 31, 2020 for corresponding Japanese Application No. 2015-151309 and English translation.
Decision of Dismissal of Amendment dated Mar. 31, 2020 for corresponding Japanese Application No. 2015-151309 and English translation.
European Office Action dated Apr. 20, 2020 for corresponding European Application No. 16830607.4.
Written Opinion dated May 16, 2020 for corresponding Singapore Application No. 11201800647S.
Chinese Office Action dated Jan. 14, 2021 for corresponding Chinese Application No. 201680044004.7 and English translation.
European Office Action dated Dec. 23, 2020 for corresponding European Application No. 16830607.4.

* cited by examiner

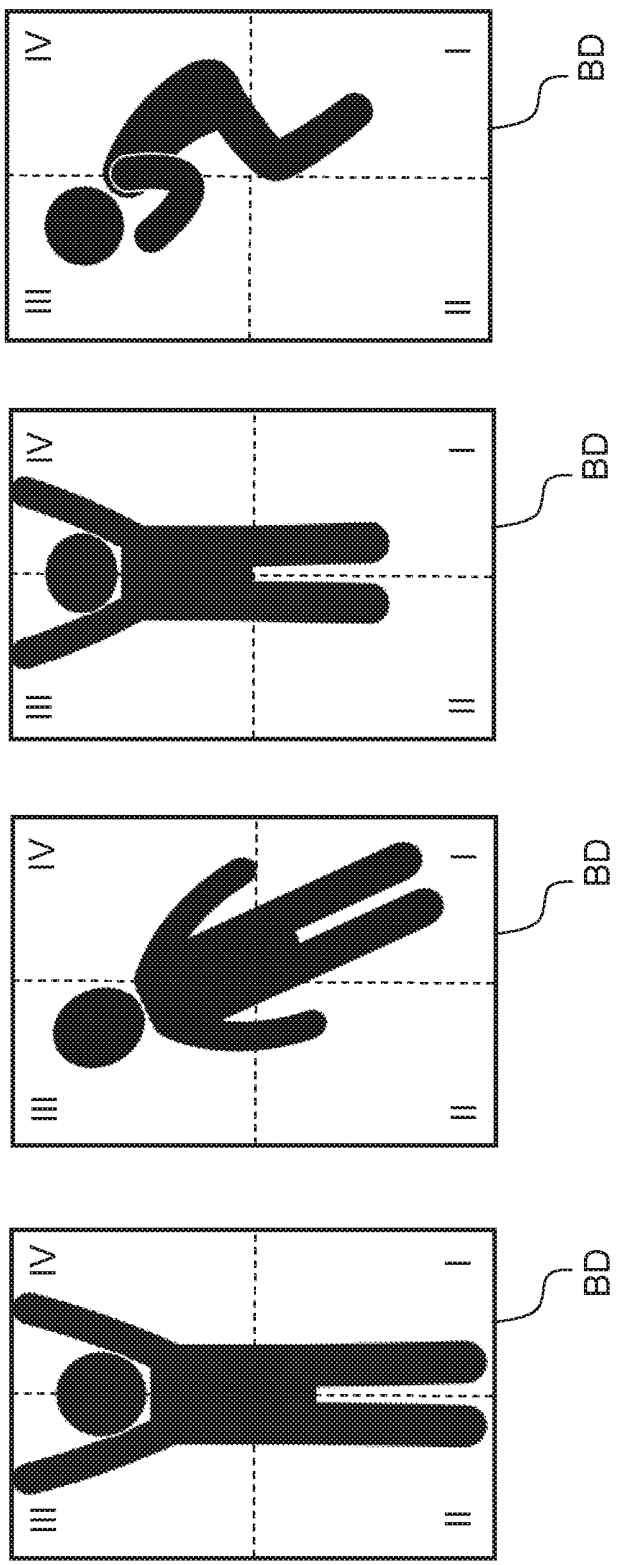

BIOLOGICAL CONDITION DETERMINING APPARATUS AND BIOLOGICAL CONDITION DETERMINING METHOD

CROSS-REFERENCE TO RELATED APPLICATIONS

This application is a Continuation Application of International Application No. PCT/JP2016/072323 claiming the conventional priority of Japanese patent Application No. 2015-151309 filed on Jul. 30, 2015, and titled "BIOLOGICAL CONDITION DETERMINATION DEVICE AND BIOLOGICAL CONDITION DETERMINATION METHOD". The disclosures of Japanese patent Application No. 2015-151309 and International Application No. PCT/JP2016/072323 are incorporated herein by reference in their entirety.

BACKGROUND

The present disclosure relates to a biological condition determining apparatus (a biological condition determination device) using load detector(s), and a biological condition determining method (a biological condition determination method) using the biological condition determining apparatus.

Systems for managing, from a remote place, patients and/or persons receiving nursing care on their beds are utilized in hospitals, care facilities and the like. For example, if a system is used in a hospital to detect a patient's present (exist, settling) on/leaving (absent) from the bed, then the nurses in the nurse station can check whether or not the patient is on the bed in his/her room without visiting the room.

Japanese Patent Application Laid-open No. 2008-49023 discloses a care support system with a sensor mat arranged on a board (support board) of the bed to detect, on the basis of an output from the sensor mat, a care receiver's settling on/leaving from the bed and/or respiration information of the care receiver such as a change in the respiratory frequency, the peak intensity of the respiratory spectrum, and the like.

Japanese Patent Application Laid-open No. 2008-264338 discloses a settle-on-bed detecting method with load detecting means arranged respectively under the four feet of a bed to determine whether or not a person is present on the bed on the basis of outputs from the load detecting means. Further, the patent literature 2 discloses that the load detecting means detect whether or not there is respiration in the person to determine whether or not the person performs respiration, thereby increasing the accuracy of the settle-on-bed detection.

SUMMARY

For the care support system disclosed in Japanese Patent Application Laid-open No. 2008-49023, it is necessary to arrange a sensor mat on the board of the bed. Because the sensor mat is comparatively expensive and has a short usable life, the running cost is high. Meanwhile, the settle-on-bed detecting system disclosed in Japanese Patent Application Laid-open No. 2008-264338 does not use a sensor mat, but can only detect whether or not there is respiration in a subject and cannot know a more detailed respiratory condition (respiratory state) of the subject.

In view of the above, an object of the present disclosure is to solve the foregoing problems and provide a biological condition determining apparatus and a biological condition determining method which are capable of easily determining, in a detailed manner, a biological condition (biological state) of a subject on the bed.

According to a first aspect of the present disclosure, there is provided a biological condition determining apparatus for determining a biological condition of a subject on a bed, the apparatus including:

a plurality of load detectors which are placed in the bed or under feet of the bed and which detect a load of the subject;

a biological information extracting unit which extracts biological information from an output of at least one of the load detectors;

a determining unit which determines the biological condition of the subject by comparing the extracted biological information with a referential information prepared beforehand; and an output unit which outputs the biological condition (biological state) of the subject determined by the determining unit.

According to a second aspect of the present disclosure, there is provided a method for determining a biological condition of a subject on a bed by using a biological condition determining apparatus, the method including:

detecting a load of the subject by using a plurality of load detectors placed in the bed or under feet of the bed;

extracting biological information from an output of at least one of the load detectors by using a biological information extracting unit; and determining the biological condition of the subject by comparing the extracted biological information with a referential information prepared beforehand, by using a determining unit.

BRIEF DESCRIPTION OF THE DRAWINGS

FIGS. 11A and 11B depict a relation between a body posture of a subject and the load signals, wherein FIG. 11A depicts the subject in a supine position (lying on his/her back), and FIG. 11B depicts exemplary load signals when the subject assumes the body posture of FIG. 11A.

FIGS. 12A and 12B depict another relation between the body posture of the subject and the load signals, wherein FIG. 12A depicts the subject in a recumbent position (lying on his/her left side of the body), and FIG. 12B depicts exemplary load signals when the subject assumes the body posture of FIG. 12A.

FIGS. 13A and 13B depict still another relation between the body posture of the subject and the load signals, wherein FIG. 13A depicts the subject in a recumbent position (lying on his/her right side of the body), and FIG. 13B depicts exemplary load signals when the subject assumes the body posture of FIG. 13A.

FIGS. 14A, 14B, 14C, and 14D depict various exemplary body postures identified by a body posture identifying unit.

EMBODIMENTS

First Embodiment

An embodiment of the present disclosure will be explained with reference to FIGS. 1 to 16.

Figure 1:
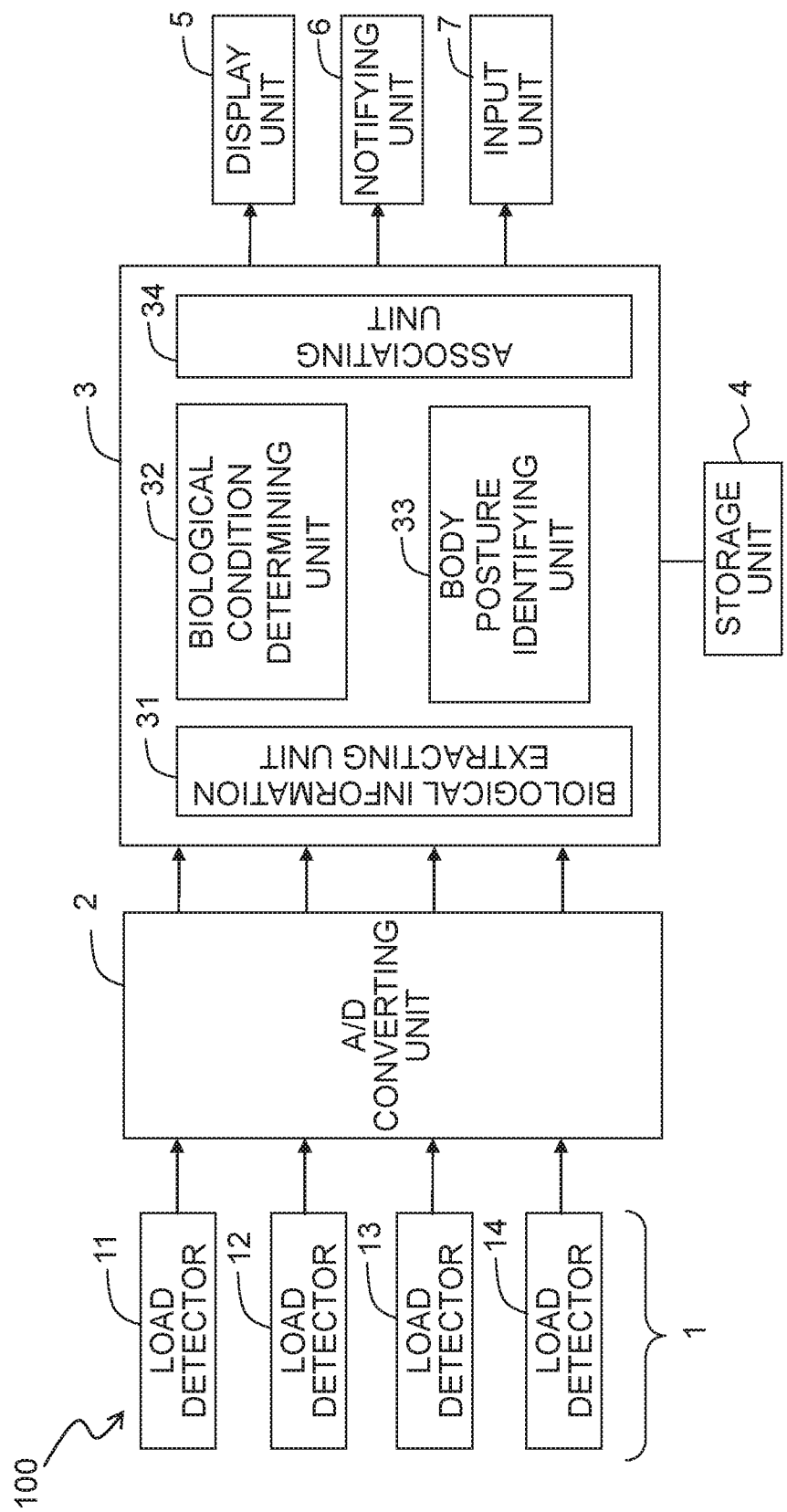
FIG. 1 is a block diagram depicting an overall configuration of a biological condition determining apparatus according to an embodiment of the present disclosure.

As depicted in FIG. 1, a biological condition determining apparatus 100 of this embodiment mainly includes a load detecting unit 1, a control unit (controller) 3, a storage unit (storage, memory) 4, and a display unit (display) 5. The load detecting unit 1 and the control unit 3 are connected via an A/D converting unit 2. The control unit 3 is further connected with a notifying unit 6 and an input unit 7.

The load detecting unit 1 is provided with four load detectors 11, 12, 13, 14. Each of the load detectors 11, 12, 13, 14 is a load detector which detects the load by using a beam-type load cell. Such a load detector is disclosed, for example, in Japanese Patent No. 4829020 and Japanese Patent No. 4002905. Each of the load detectors 11, 12, 13, 14 is connected to the A/D converting unit 2 by means of wiring.

The A/D converting unit 2 is provided with an A/D converter which converts the analog signal fed from the load detecting unit 1 into the digital signal. The A/D converting unit 2 is connected to each of the load detecting unit 1 and the control unit 3 by means of wiring.

The control unit 3 is an exclusive or general-purpose computer. A biological information extracting unit 31, a biological condition determining unit 32, a body posture identifying unit 33, and an associating unit 34 are constructed therein.

The storage unit 4 is a storage device which stores the data used for the biological condition determining apparatus 100. For example, it is possible to use a hard disk (magnetic disk), a semiconductor memory, or the like therefor. The display unit 5 is a monitor such as a liquid crystal monitor or the like for displaying the information outputted from the control unit 3 for a user of the biological condition determining apparatus 100.

The notifying unit 6 is provided with a device for visually or auditorily performing predetermined notification on the basis of the information fed from the control unit 3, for example, a speaker. The input unit 7 is an interface for performing predetermined input for the control unit 3, which may be a keyboard and a mouse.

Next, an explanation will be made about the operation for determining a biological condition (condition or state of a living body) of a subject (human subject) on the bed and identifying a body posture (body position) of the subject, by using the biological condition determining apparatus 100.

Figure 2:
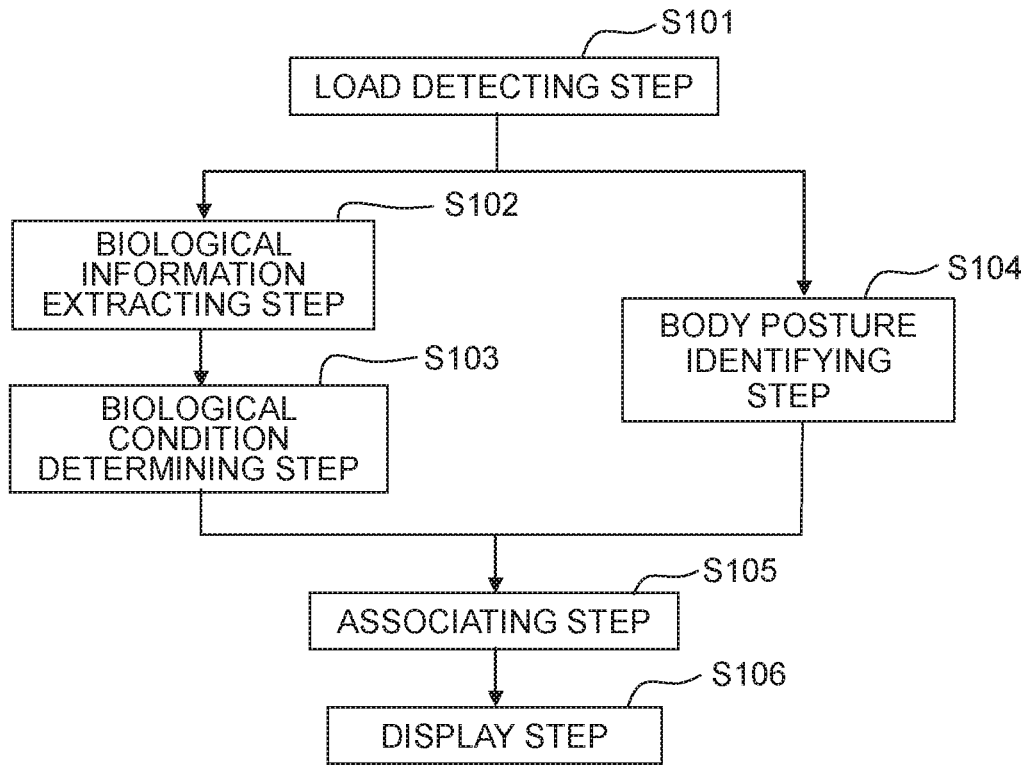
FIG. 2 is a flow chart depicting an operational flow of the biological condition determining apparatus.

As depicted in FIG. 2, the determination of a biological condition of a subject S and the identification of a body posture of the subject (human subject) S, which are based on the use of the biological condition determining apparatus 100, include a load detecting step (S101), a biological information extracting step (S102), a biological condition determining step (S103), a body posture identifying step (S104), an associating step (S105), and a display step (S106). The load detecting step (S101) is a step of detecting the load of the subject S. The biological information extracting step (S102) is a step of extracting (taking out), from the detected load, information about a living body (particularly, information about respiration) of the subject and information about a body posture of the subject. The biological condition determining step (S103) is a step of determining a biological condition (particularly, respiratory condition) of the subject S on the basis of the extracted biological information. The body posture identifying step (S104) is a step of identifying the body posture of the subject S based on the detected load. The associating step (S105) is a step of associating the biological condition of the subject determined in the biological condition determining step with the body posture of the subject identified in the body posture identifying step so as to create biological condition information. The display step (S106) is a step of displaying the obtained biological condition information.

<Load Detecting Step>

Figure 3:
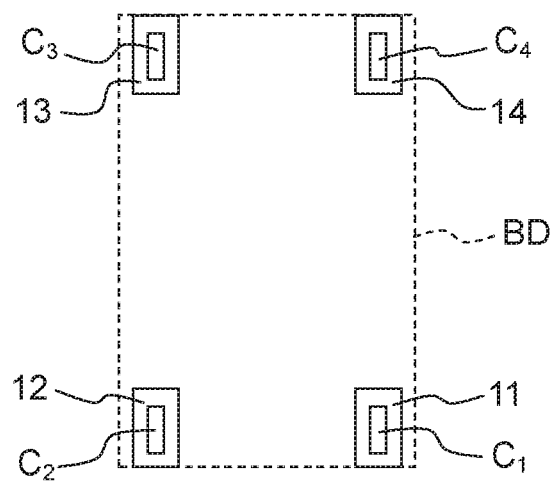
FIG. 3 is an illustrative view depicting an arrangement of load detectors with respect to a bed.

In order to perform the load detecting step S101, the four load detectors 11, 12, 13, 14 of the load detecting unit 1 are arranged under the feet (legs) of a bed to be used by the subject. Specifically, as depicted in FIG. 3, the load detectors 11, 12, 13, 14 are arranged respectively under casters $C_1$, $C_2$, $C_3$, $C_4$ attached to lower end portions of the feet (legs) disposed at the four corners of the bed BD.

Figure 4:
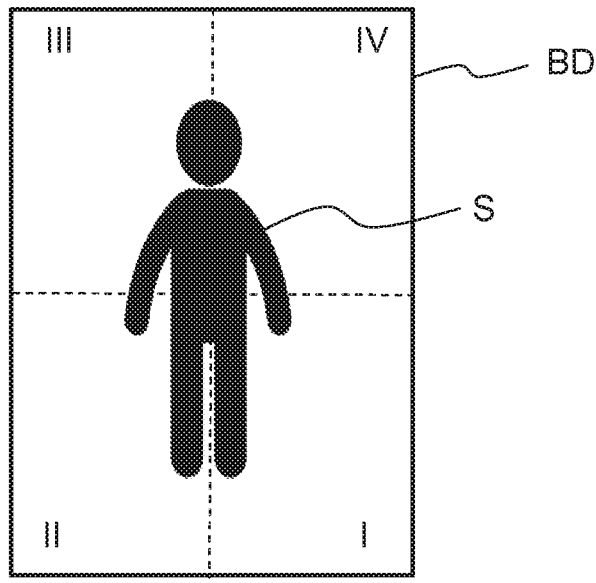
FIG. 4 is an illustrative view depicting an arrangement of four load detection areas defined on the upper surface of the bed.

When the load detectors 11, 12, 13, 14 are arranged under the casters $C_1$, $C_2$, $C_3$, $C_4$ respectively, the load, which is applied to the upper surface of the bed BD, is thereby detected in a dispersed manner by the four load detectors 11, 12, 13, 14. Specifically, as depicted in FIG. 4, the rectangular upper surface of the bed BD is longitudinally divided into two and laterally divided into two, and thus the upper surface is equally divided into four rectangular areas I to IV. Accordingly, the load, which is applied to the area I positioned with the left lower half of the body of the subject S lying on his/her back (face up, that is in the supine position) in a central portion of the bed BD, is detected principally by the load detector 11, and the load, which is applied to the area II positioned with the right lower half of the body of the subject S in the same state, is detected principally by the load detector 12. Similarly, the load, which is applied to the area III positioned with the right upper half of the body of the subject S lying on his/her back in the central portion of the bed BD, is detected principally by the load detector 13, and the load, which is applied to the area IV positioned with the left upper half of the body of the subject S in the same state, is detected principally by the load detector 14.

Each of the load detectors 11, 12, 13, 14 detects the load once in every 0.1 second, for example, and outputs an analog signal containing the load information to the A/D converting unit 2. The A/D converting unit 2 converts the received analog signal into the digital signal. The digital signal containing the load information (to be referred to hereinafter as "load signal") is outputted to the control unit 3.

Figure 5:
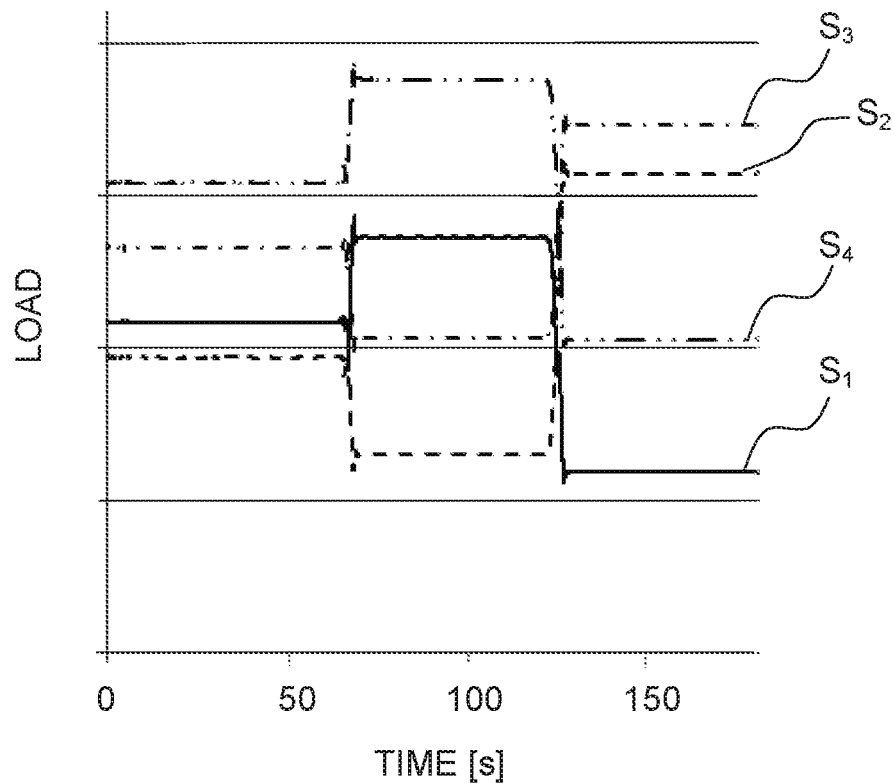
FIG. 5 depicts exemplary load signals outputted from the load detectors.

FIG. 5 depicts exemplary load signals sent from the A/D converting unit 2 to the control unit 3. The load signals include four signals: a load signal $S_1$ (solid line) outputted from the load detector 11, a load signal $S_2$ (broken line) outputted from the load detector 12, a load signal $S_3$ (alternate long and short dash line) outputted from the load detector 13, and a load signal $S_4$ (alternate long and two short dashes line) outputted from the load detector 14. Each of the load signals $S_1$, $S_2$, $S_3$, $S_4$ outputted from the load detectors 11, 12, 13, 14 contains a signal containing respiration information of the subject S and a signal containing body posture information of the subject S. According to the present disclosure, the signal containing the respiration information is focused on and treated (considered) as the signal exhibiting the biological condition. This will be described in detail later on.

<Biological Information Extracting Step>

In the biological information extracting step S102, a biological information extracting unit 31 constructed inside the control unit 3 receives a load signal sent from the A/D converting unit 2; separates, from the received load signal, a signal containing biological information of the subject S (to be referred to below simply as "respiration information" or "respiration signal"); and extracts the same.

Firstly a detailed explanation will be made about the load signal sent from the A/D converting unit 2.

The load signal sent from the A/D converting unit 2 containing the respiration information and the body posture information as described earlier on. An origin of the respiration information contained in the load signal is a change in the center of gravity position of the subject S which changes with the respiration of the subject S. That is, when the subject S respires, then the diaphragm of the subject S moves, and accordingly, internal organs of the subject S move. Hence, the center of gravity position of the subject S moves such that a slight change occurs in the value of the load applied by the subject S on each of the load detectors 11, 12, 13, 14. In the same manner, an origin of the body posture information contained in the load signal is a change in the value of the load applied on each of the load detectors 11, 12, 13, 14 according to the change in the body posture of the subject S.

Specifically, in FIG. 5, in the interval depicted leftmost (the interval of the time 0 second to 60 seconds), the subject S is observed as in the supine position (FIG. 4) with his/her arms and legs stretching out in the center of the bed BD. On this occasion, a comparatively large value is assigned to each of the signal $S_4$ outputted from the load detector 14 and the signal $S_3$ outputted from the load detector 13 whereas a comparatively small value is assigned to each of the signal $S_1$ outputted from the load detector 11 and the signal $S_2$ outputted from the load detector 12. Further, in FIG. 5, in the interval depicted rightmost (the interval of the time 120 seconds to 180 seconds), the subject S is observed with his/her upper half of the body in the area III of the bed BD and with his/her lower half of the body in the area II. On this occasion, a comparatively large value is assigned to each of the signal $S_3$ outputted from the load detector 13 and the signal $S_2$ outputted from the load detector 12 whereas a comparatively small value is assigned to each of the signal $S_1$ outputted from the load detector 11 and the signal $S_4$ outputted from the load detector 14. That is, it is understood that the balances between the values of the load signals $S_1$ to $S_4$ fed from the load detectors 11 to 14 are the body posture information, i.e., the signal changing with the body posture of the subject S on the bed BD.

On the other hand, the respiration information is not present in FIG. 5 at a visible scale. This is because the respiration information is ascribed to a slight change of the center of gravity with the respiration of the subject S, and the fluctuation range of the load value is far smaller than the whole magnitude of the load signal.

According to the method of the present disclosure, it is possible to extract, from the load signal, the respiration information far smaller than the whole magnitude of the load signal. It is known that the human being has about 12 to 20 respirations per minute. This is about 3 seconds to 5 seconds when converted into period, or about 0.2 Hz to 0.33 Hz when converted into frequency. On the other hand, the human being does not periodically change his/her body posture, and thus, it is difficult to assume that the subject S in sleep on the bed changes his/her body posture successively with a period not longer than 5 seconds (at a frequency of 0.2 Hz or above). Therefore, it is conceivable that among the load signals, those varying in the range from about 0.2 Hz to 0.33 Hz have the respiration information whereas those varying in a range less than 0.2 Hz have the body posture information. Hence, it is possible to extract the respiration information from the load signals, by extracting, from the load signal, the signal ranging from 0.2 Hz to 0.33 Hz.

Specifically for example, the respiration information is extracted from the load signals by performing Fourier transform, frequency filter process, and/or inverse Fourier transform for the load signals, and extracting waveforms with the frequency ranging from about 0.2 Hz to about 0.33 Hz.

Figure 6:
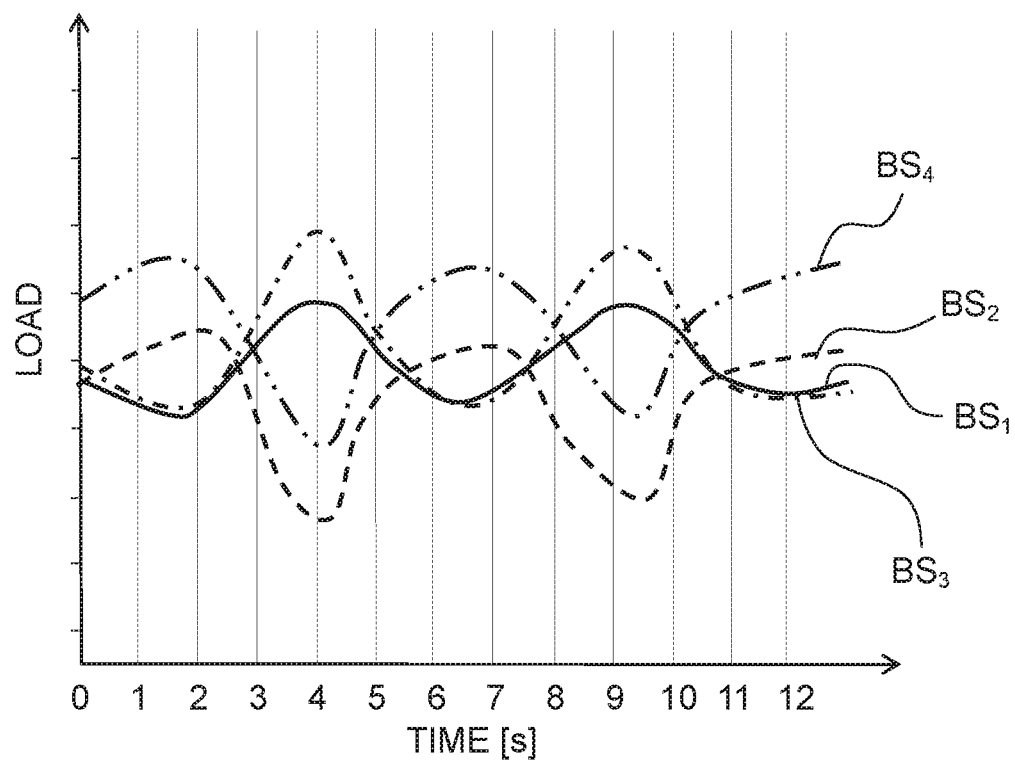
FIG. 6 depicts exemplary respiration information extracted (taken out) from the load signals.

FIG. 6 depicts the respiration information $BS_1$ to $BS_4$ over 13 seconds extracted, via the above steps, from the interval of 0 second to 60 seconds of the load signals $S_1$ to $S_4$ depicted in FIG. 5. In FIG. 6, respiration information $BS_1$ to $BS_4$ vary with a period of about 4 to 5 seconds according to the change of the load applied to the areas I to IV. Further, in each of the respiration information $BS_1$ to $BS_4$ depicted in FIG. 6, the influence of the body posture (the DC component in FIG. 5) is completely removed.

Among the extracted respiration information $BS_1$ to $BS_4$, the information (signals) having the waveform with the largest amplitude is conceived to have a high reliability. Thus, the biological information extracting unit 31 selects such information (signal) from the extracted respiration information $BS_1$ to $BS_4$, and sends the same to the biological condition determining unit 32.

<Biological Condition Determining Step>

In the biological condition determining step S103, the biological condition determining unit 32 constructed inside the control unit 3 receives the respiration information from the biological information extracting unit 31, compares this respiration information to referential information stored in the storage unit 4, and determines the respiratory condition (respiratory state) of the subject S.

The storage unit 4 stores, as the referential information, respiration information denoting various respiratory conditions of the subject S. One example is ordinary respiration information denoting the subject S respiring ordinarily, snore information denoting the subject snoring, and apnea information denoting the subject S in an apneic state.

Figure 7:
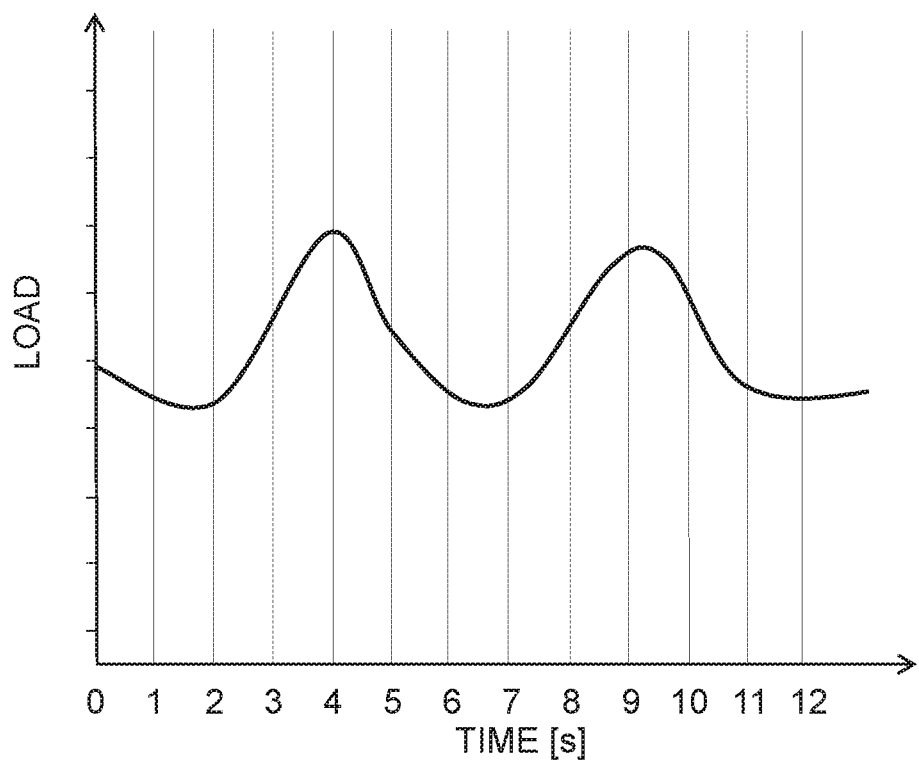
FIG. 7 is a waveform chart depicting exemplary respiration information corresponding to an ordinary respiratory state.
Figure 8:
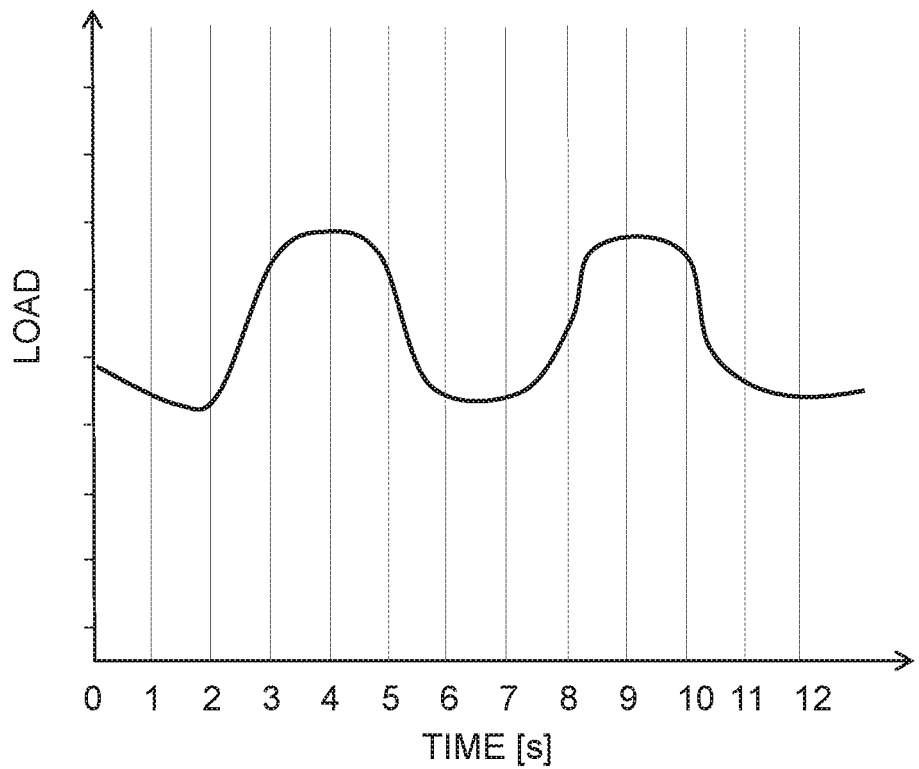
FIG. 8 is a waveform chart depicting exemplary respiration information corresponding to a snoring state.
Figure 9:
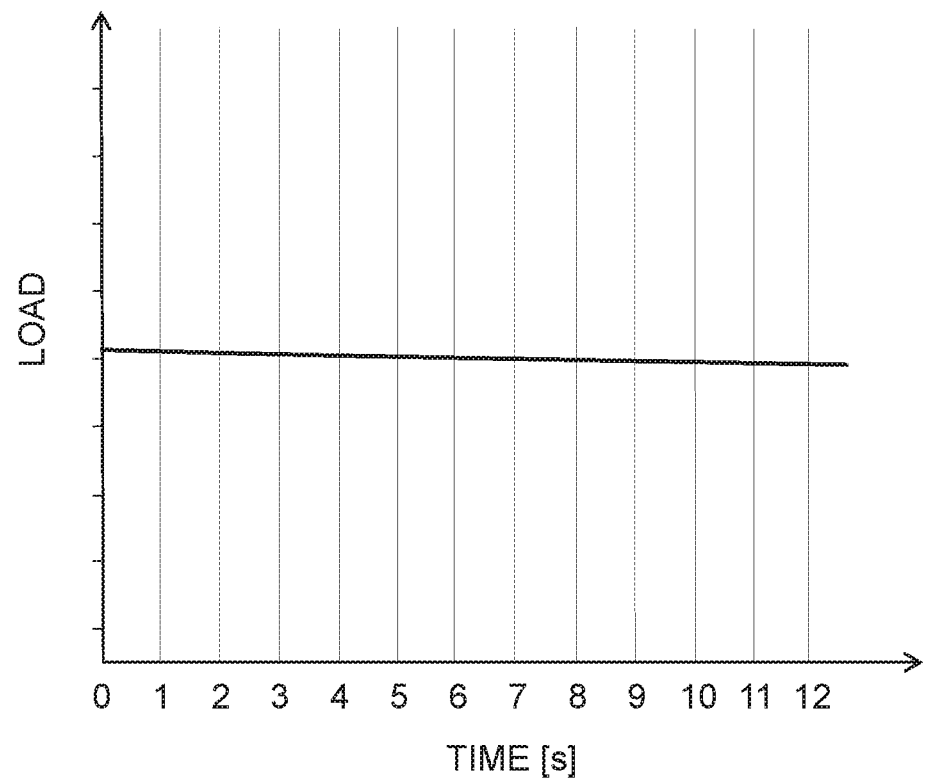
FIG. 9 is a waveform chart depicting exemplary respiration information corresponding to an apneic state.

The ordinary respiration information is stored as a waveform depicted in FIG. 7, for example. The ordinary respiration information has a form close to a sine wave. The snore information is stored as a waveform depicted in FIG. 8, for example. The waveform corresponding to the snore information is closer to a rectangular wave than the waveform corresponding to the ordinary respiration information is. The apnea information is stored with the form depicted in FIG. 9, for example.

Figure 10:
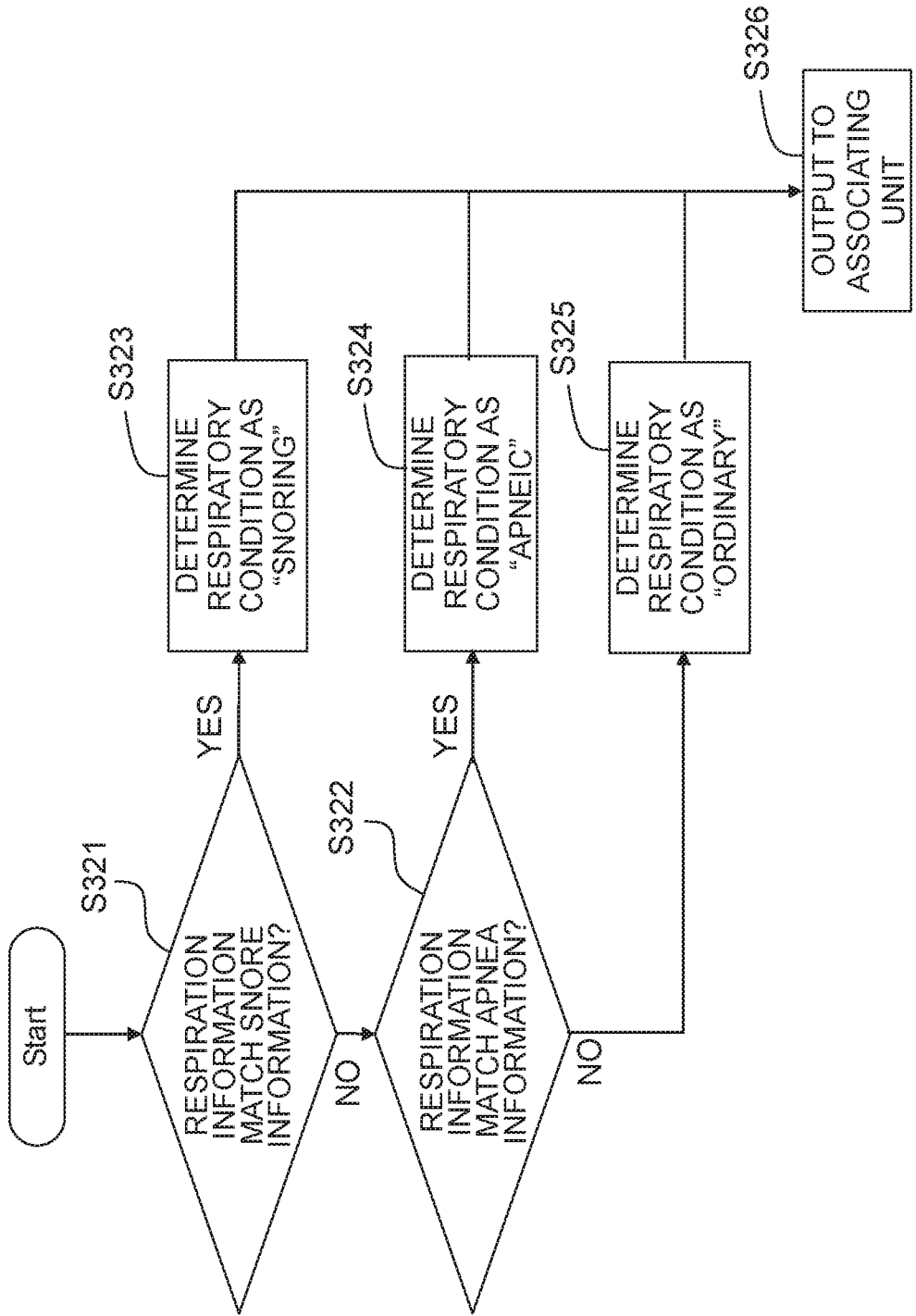
FIG. 10 is a flow chart depicting an exemplary respiratory condition determining operation performed by a biological condition determining unit.

FIG. 10 depicts an exemplary procedure for the biological condition determining unit 32 to determine the respiratory condition of the subject S. The biological condition determining unit 32 first compares the respiration information received from the biological information extracting unit 31 to the snore information stored in the storage unit 4, and determines whether or not the two waveforms thereof match or resemble each other (S321). This determination can be performed by, for example, obtaining a correlation function for the two waveforms and comparing the correlation function to a threshold value.

If the respiration information matches or resembles the snore information (S321: "Yes"), then the biological condition determining unit 32 determines that the respiratory condition of the subject S is "snoring" (S323), and sends the determination result to the associating unit 34 (S326). If the respiration information neither matches nor resembles the snore information (S321: "No"), then the biological condition determining unit 32 proceeds to the step S322.

In the step S322, the biological condition determining unit 32 compares the respiration information received from the biological information extracting unit 31 to the apnea information stored in the storage unit 4, and determines whether or not the two pieces of information match or resemble each other (S322). This determination is performed by the same method as that in the step S321.

If the respiration information matches or resembles the apnea information (S322: "Yes"), then the biological condition determining unit 32 determines that the respiratory condition of the subject S is "apneic" (S324), and sends the determination result to the associating unit 34 (S326). If the respiration information neither matches nor resembles the apnea information (S322: "No"), then the biological condition determining unit 32 determines that the respiratory condition of the subject S is "ordinary" (S325), and sends the determined result to the associating unit 34 (S326).

In this embodiment, the determination is performed to discern the respiratory conditions between the ordinary, apneic and snoring states. However, without being limited to that, it is also possible to determine whether the subject is alive or not, and whether the subject is in a pathological condition or not, on the basis of the respiration information.

<Body Posture Identifying Step>

In the body posture identifying step S104, the body posture identifying unit 33 constructed inside the control unit 3 receives the body posture information from the biological information extracting unit 31 and identifies the body posture of the subject S on the bed BD.

The biological information extracting unit 31 sends the load signal received from the A/D converting unit 2 as it is to the body posture identifying unit 33, as the body posture information. As described earlier on, because the body posture information is detected with the magnitude of a far higher order than the respiration information, even if the load signal containing the respiration information is used as it is, as the body posture information, there is no influence exerted on identifying the body posture.

The body posture identifying unit 33 identifies the body posture of the subject S in such a specific manner as follows.

As described earlier on, the load detectors 11, 12, 13, 14 detect the load applied on the bed BD as four loads divided via the four areas I to IV. Therefore, if the subject S on the bed BD changes his/her body posture, then each of the load applied to the area I, area II, area III and area IV changes and consequently, the values detected by the load detectors 11, 12, 13, 14, i.e., the load signals change. The body posture identifying unit 33 identifies the body posture of the subject S on the basis of the load signals $S_1$ to $S_4$ received from the biological information extracting unit 31, and a prestored corresponding relation between a combination of load signals and the body posture of the subject S.

Figure 11A:
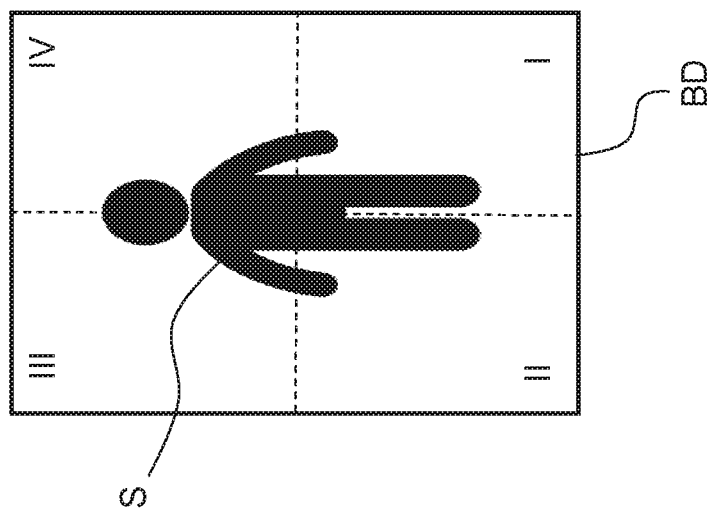
Figure 11B:
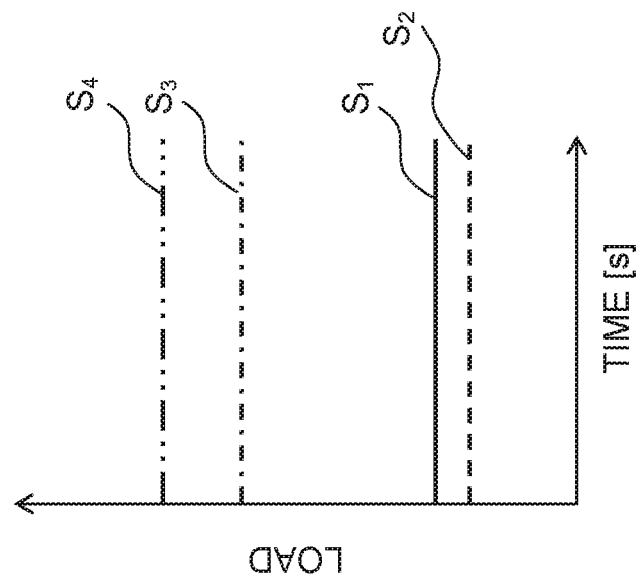

For example, the body posture identifying unit 33 stores a combination of the load signals $S_1$ to $S_4$ depicted in FIG. 11B and the body posture of the subject S depicted in FIG. 11A (in the supine position in a central portion of the bed with his/her arms and legs stretching out straightly), in a manner that they are associated with each other. Therefore, if the load signals sent from the biological information extracting unit 31 have the shapes or values depicted in FIG. 11B or have the shapes or values similar to those depicted in FIG. 11B, then it is identified that the subject S assumes the body posture of "in the supine position in a central portion of the bed with his/her arms and legs stretching out straightly".

Figure 12A:
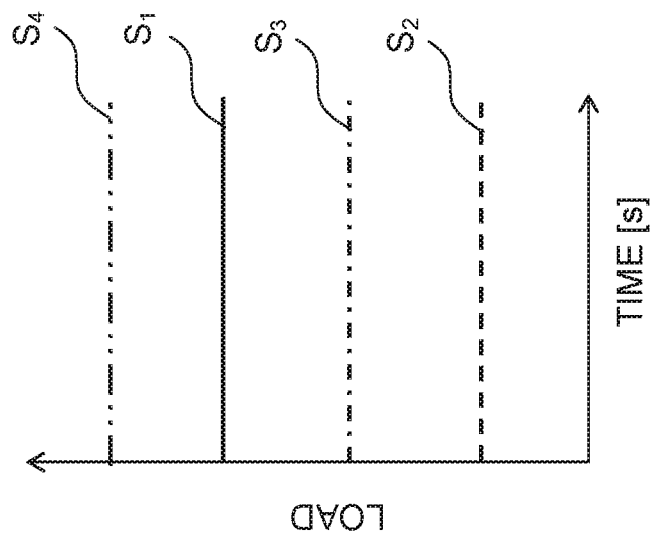
Figure 12B:
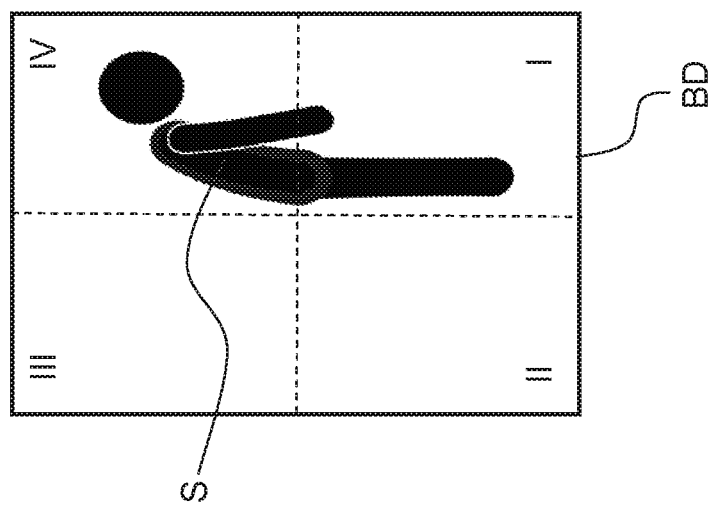

Likewise, the body posture identifying unit 33 stores a combination of the load signals $S_1$ to $S_4$ depicted in FIG. 12B and the body posture of the subject S depicted in FIG. 12A (in the recumbent position (lying sideways) on his/her left side of the body in the area I and the area IV), in a manner that they are associated with each other. Therefore, if the load signals sent from the biological information extracting unit 31 have the shapes or values depicted in FIG. 12B or have the shapes or values similar to those depicted in FIG. 12B, then it is identified that the subject S assumes the body posture of "in the recumbent position on his/her left side of the body in the area I and the area IV)".

Figure 13A:
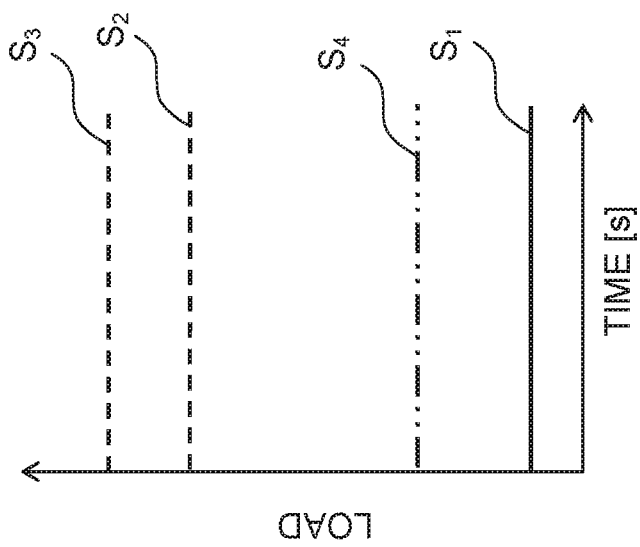
Figure 13B:
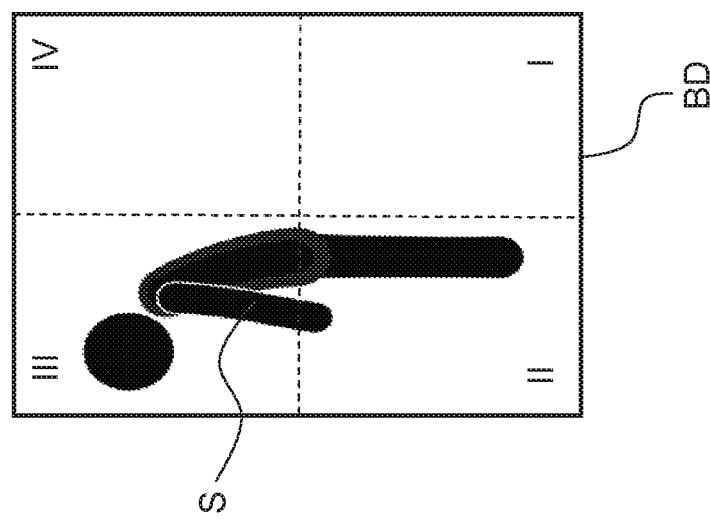

Further, the body posture identifying unit 33 stores a combination of the load signals $S_1$ to $S_4$ depicted in FIG. 13B and the body posture of the subject S depicted in FIG. 13A (in the recumbent position on his/her right side of the body in the area II and the area III), in a manner that they are associated with each other. Therefore, if the load signals sent from the biological information extracting unit 31 have the shapes or values depicted in FIG. 13B or the shapes or values similar to those depicted in FIG. 13B, then it is identified that the subject S assumes the body posture of "in the recumbent position on his/her right side of the body in the area II and the area III)".

In addition, the body posture identifying unit 33 stores the combination of the load signals $S_1$ to $S_4$ correspondingly with each of various body postures such as described below. That is, a body posture of the supine position in the central portion of the bed with the legs stretching out and the arms stretching out so that the hands are placed on the upper side of the head (FIG. 14A), a body posture of the tilted prone position (lying face down) with the head positioned in the area III and the legs in the area I (FIG. 14B), a body posture of the supine position in a central portion of the bed with the knees bending and the arms stretching out so that the hands are placed on the upper side of the head (FIG. 14C), a body posture of the recumbent position with the body curled up to place the head in the area III, the trunk in the area IV and the legs in the area I, etc. Therefore, it is possible to identify various body postures of the subject S on the basis of the load signal sent from the biological information extracting unit 31, and the stored corresponding relation.

The body posture of the subject S identified by the body posture identifying unit 33 is sent to the associating unit 34.

<Associating Step>

In the associating step S105, the associating unit 34 constructed inside the control unit 3 associates the respiratory condition of the subject S received from the biological condition determining unit 32 with the body posture of the subject S received from the body posture identifying unit 33.

For example, in the step of creating sleeping condition (sleeping state) information, the associating unit 34 associates the respiratory condition of the subject S received from the biological condition determining unit 32 with the body posture of the subject S received from the body posture identifying unit 33, with time (clock time, or passage of time from the beginning of detection) as the mediator, and creates the sleeping condition information which is a combination of respiratory condition and body posture. The created sleeping condition information is sent to the display unit 5.

<Display Step>

In the display step S106, the display unit 5 visually displays the sleeping condition information received from the control unit 3 (the associating unit 34).

Figure 15:
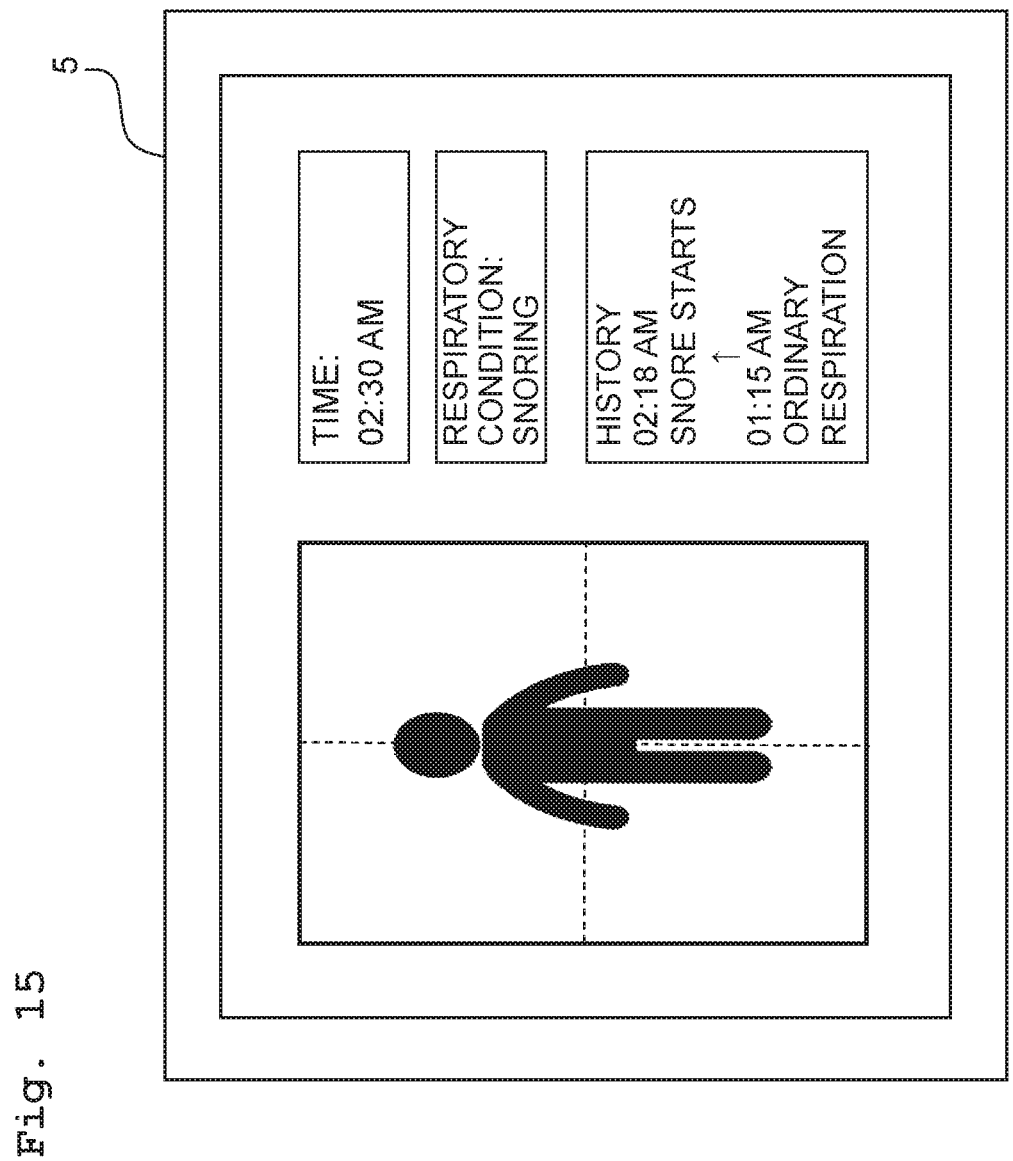
FIG. 15 depicts exemplary information displayed on a display unit.

As depicted in FIG. 15, the body posture of the subject S is displayed with an image on the monitor of the display unit 5. Therefore, the user can intuitively grasp the body posture of the subject S by merely viewing the display unit 5. Further, it is also possible for the user to video-record (record) a body posture image of the subject S in the storage unit 4.

For diagnosis of sleep apnea syndrome (SAS), although overnight video-recording of the body posture of sleeping patients is also performed with patients staying in a medical institution, many patients exhibit a certain disinclination against the video-recording of their sleeping forms and/or sleeping faces. However, by using the display unit 5 of the present disclosure, no sleeping face will be video-recorded and the sleeping form is recorded as a silhouette at a high anonymity such that it is possible to provide more patients with the opportunity for the diagnosis.

In addition, on the monitor of the display unit 5, there are also displayed the current time, the respiratory condition of the subject S, and the history of the respiratory condition of the subject S. Further, the display unit 5 may also display the respiratory period of the subject S, the number of times of having fallen into the apneic state since one hour ago, and the like.

The user can also set the system to cause the notifying unit 6 to notify the user if the subject S comes into a predetermined condition. For example, it is possible for the user to set the system such that if the subject S has come into the apneic state five times or more during one hour period, then it is notified.

A summarization will be made below about the effects of the biological condition determining apparatus 100 of this embodiment.

The biological condition determining apparatus 100 of the embodiment extracts the respiration information as a waveform from the load signals, compares the same to the prestored referential information, and determines the respiratory condition of the subject S. Therefore, it is possible to satisfactorily determine various respiratory conditions of the subject S such as the ordinary respiratory state, the snoring state, the apneic state, and the like. Further, by improving or enhancing the types of referential information, it is possible not only to increase the accuracy of the determination but also to identify the respiratory condition of the subject S in a detailed manner.

The biological condition determining apparatus 100 of the embodiment identifies the body posture of the subject S on the basis of a prestored corresponding relation between a combination of the detected values fed from the load detecting unit 1, and the body posture of the subject S. Therefore, it is possible to satisfactorily identify various body postures of the subject S on the bed BD. Further, by improving or enhancing the prestored corresponding relation, it is possible not only to increase the accuracy of the identification but also to identify the body posture more definitely or exactly.

The biological condition determining apparatus 100 of the embodiment can graphically display the body posture (sleeping form) of the subject S in sleep, and video-record the same. Therefore, for the patients who exhibit the disinclination against video-recording their sleeping appearances for diagnosing purpose, it is also possible to provide them with the opportunity of appropriate diagnosis and treatment without bringing on the disinclination.

The biological condition determining apparatus 100 of the embodiment lets the associating unit 34 associate the respiratory condition of the subject S and body posture of the subject S with each other so as to create the sleeping condition information, and lets the display unit 5 display the same. Therefore, it is possible to satisfactorily present the user with a relationship between the body posture of the subject S and the respiratory condition of the subject S. Using this relationship, the doctor can conduct a study on the respiratory condition of the subject S based on the relation between the respiratory condition and the body posture, and/or give advice about the body posture in sleep suitable for keeping a good respiratory condition.

Next, regarding the biological condition determining apparatus 100 of the this embodiment, an explanation will be made about a method for preparing the referential information used for the biological condition determining unit 32 to determine the respiratory condition of the subject S.

While it is possible to prepare the referential information by various methods, a first exemplary method is to collect, from a number of subjects S, respiration information (waveform) in ordinary respiration, respiration information (waveform) during snoring, respiration information (waveform) in apnea and, based on those pieces of information, create referential ordinary respiration information, referential snore information, and referential apnea information. The referential ordinary respiration information has such a virtual waveform as described below. That is, the virtual waveform is determined by the biological condition determining unit 32 as "matching" all pieces of the ordinary respiration information, each having individual difference, collected from the multiple subjects. This is also true to the referential snore information and the referential apnea information. In this manner, by using the same referential information for all subjects S, it is possible to reduce the volume of information stored in the storage unit 4.

If it is desired for the biological condition determining unit 32 to further reliably determine the respiratory condition, then it is possible to divide the subjects S into groups according to various attributes, and prepare the referential information according to each group. Exemplary attributes used therefor are sex, age, body height, body weight, average respiratory rate at rest, average pulse rate at rest, etc. In addition, it is also allowable to divide the subjects S according to whether or not they have some previous diseases (especially those related to respiratory diseases) and/or whether or not they are diagnosed as sleep apnea syndrome.

Then, when the biological condition determining apparatus 100 is in use, the attributes of the subject S are input via the input unit 7 before determining the respiratory state of the subject S. For example, if the subject S has attributes of "Sex"=Male, "Age"=40, "Body Height"=170 cm, "Body Weight"=60 kg, "Average Respiratory Rate At Rest"=13/min, "Average Pulse Rate At Rest"=70/min, "Previous Diseases"=None, and "SAS Diagnosis"=None, then those attributes are inputted beforehand to the biological condition determining apparatus 100. With this, the biological condition determining unit 32 uses the referential information satisfying the above attributes to perform the biological condition determining step.

A second exemplary method for preparing the referential information is to collect the referential information from the subject S himself/herself. Specifically, it is as follows. By fitting respiration sensors to the nose, mouth, chest and the like of the subject S, it is possible to determine the respiratory condition of the subject S without using the biological condition determining apparatus 100 of the embodiment. Therefore, by using the respiration sensors and the biological condition determining apparatus 100 of the embodiment together over a certain time period, and comparing the respiration information obtained by the biological condition determining apparatus 100 of the embodiment to the detected result of the respiration sensors, it is possible to prepare the unique referential information for the subject S. This method is advantageous when it is desired to perform further reliable determination for the subject S who needs determination of his/her respiratory condition performed by the biological condition determining apparatus 100 of the embodiment successively (for a certain duration).

Modified Embodiment

Figure 16:
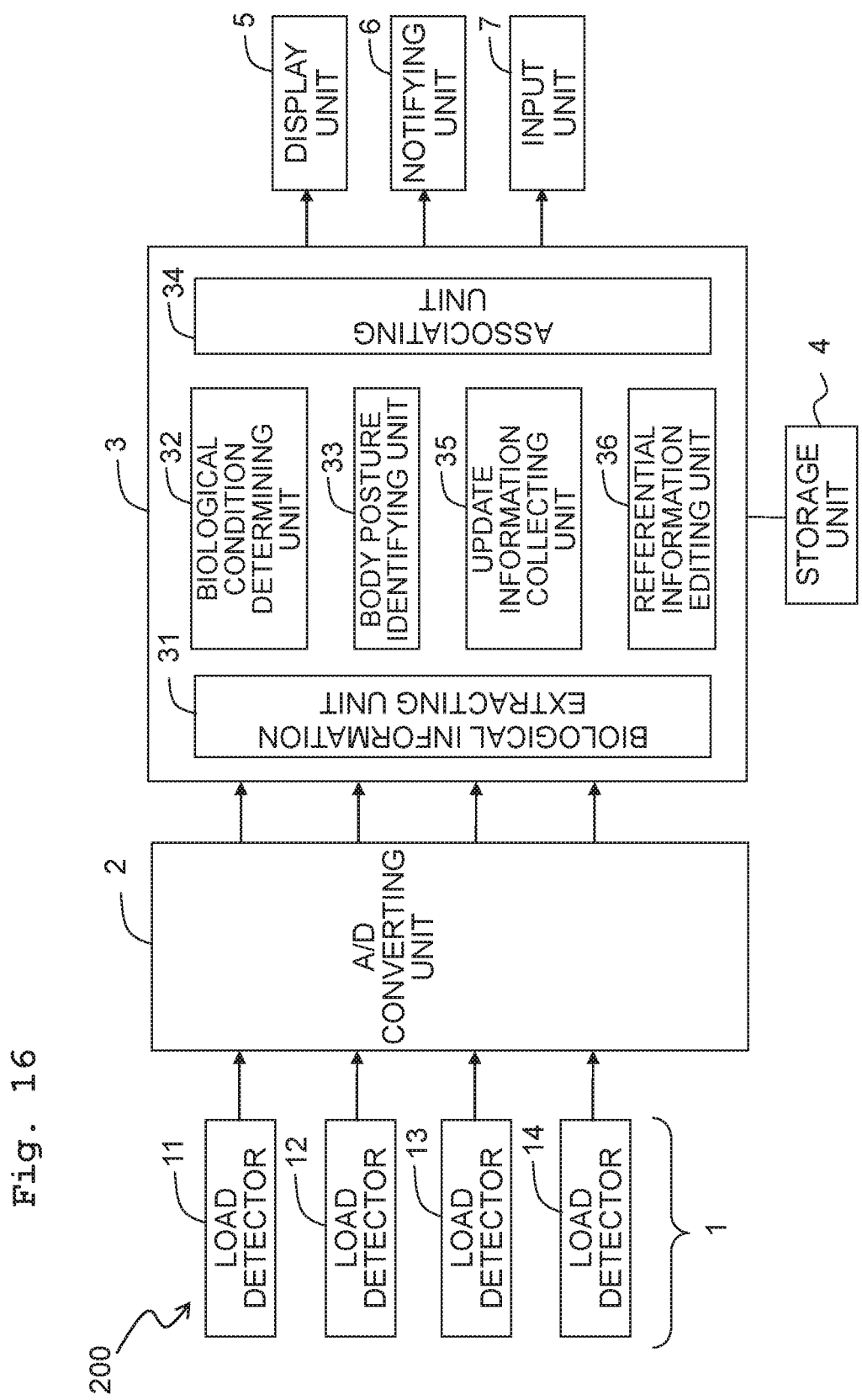
FIG. 16 is a block diagram depicting an overall configuration of a biological condition determining apparatus according to a modified embodiment of the present disclosure.

Next, referring to FIG. 16, a biological condition determining apparatus 200 according to a modified embodiment will be explained. The biological condition determining apparatus 200 of the modified embodiment is different from the biological condition determining apparatus 100 of the embodiment in that the control unit 3 is constructed to further include an update information collecting unit 35 and a referential information editing unit 36.

The update information collecting unit 35 collects new update information each time the biological condition determining apparatus 200 is used for a new subject S. Specifically, after the biological condition determining unit 32 determines that the respiratory condition of the subject S is any of the ordinary respiratory state, the snoring state and the apneic state, the update information collecting unit 35 receives the respiration information of the subject S used for the determination, and sends the same to the storage unit 4 as the update information corresponding to the determination result. That is, if the determination result is the ordinary respiratory state, the respiration information of the subject S used for the determination is sent to the storage unit 4 as the ordinary respiration information. Similarly, if the determination result is the snoring state, the respiration information used for the determination is sent to the storage unit 4 as the snore information, and if the determination result is the apneic state, the respiration information used for the determination is sent to the storage unit 4 as the apnea information.

If the attributes of the subject S (sex, age and the like) have been inputted to the biological condition determining apparatus 200, then the update information collecting unit 35 also sends the attributes of the subject S to the storage unit 4.

The referential information editing unit 36 improves the referential information already stored in the storage unit 4 on the basis of the new update information sent from the update information collecting unit 35.

According to the biological condition determining apparatus 200 of the modified embodiment, it is possible to improve or enhance the referential information while using the biological condition determining apparatus 200 in the field.

Note that in the embodiment described above, each of the load detectors 11, 12, 13, 14 is not limited to the load sensor having the beam-type load cell. It is also possible to use, for example, a force sensor.

Note that in the embodiment described above, the number of load detectors is not limited to four. It is also allowable to use five or more load detectors by providing an additional foot or additional feet for the bed BD. Alternatively (as another option), it is also allowable to arrange the load detectors for only two or three of the feet of the bed BD.

Note that in the embodiment described above, the load detectors 11, 12, 13, 14 are arranged respectively under the casters $C_1$, $C_2$, $C_3$, $C_4$ attached to the lower ends of the feet of the bed BD. However, there is no limitation thereto. Each of the load detectors 11, 12, 13, 14 may be provided respectively between one of the four feet of the bed BD and the board of the bed BD. Alternatively, if each of the four feet of the bed BD can be divided into upper and lower portions, each of the load detectors 11, 12, 13, 14 may be provided between the upper foot portion and the lower foot portion. In this specification, the "load detectors placed in the bed" mean the load detectors each of which is provided between one of the four feet of the bed BD and the board of the bed BD and the load detectors each of which is provided between the upper foot portion and the lower foot portion, as described above.

Note that in the embodiment described above, it is also allowable to provide a signal amplifying unit for amplifying the load signal fed from the load detecting unit 1 and/or a filtering unit for removing the noise from the load signal, between the load detecting unit 1 and the A/D converting unit 2.

Note that in the embodiment described above, the biological condition determining unit 32 determines that the respiratory condition of the subject S is any of the ordinary respiratory state, the snoring state and the apneic state. However, without being limited to that, the biological condition determining unit 32 may perform a more detailed determination. For example, the biological condition determining unit 32 may determine that the subject S has had any of cough, sneeze, yawn and hiccup, that the subject S is in utterance, or that the subject S is laughing. On this occasion, the storage unit 4 stores referential information denoting the cough, sneeze, yawn, hiccup, and/or referential information denoting the subject S being in utterance or laughing.

Further, in the embodiment described above, the biological information extracting unit 31 sends the load information as it is to the body posture identifying unit 33. However, the biological information extracting unit 31 may obtain a difference between the load information and the respiration information and send the obtained difference as the body posture information to the body posture identifying unit 33.

Further, in the embodiment described above, the biological information extracting unit 31 selects only the information (signal) with the largest amplitude among the respiration information $BS_1$ to $BS_4$ extracted from the signals $S_1$ to $S_4$, and sends the same to the biological condition determining unit 32. However, without being limited to that, the biological information extracting unit 31 may, for example, either select only two pieces with a larger amplitude among the respiration information $BS_1$ to $BS_4$ and send them to the biological condition determining unit 32, or send more than one piece of the respiration information $BS_1$ to $BS_4$ as they are to the biological condition determining unit 32. Having received a plurality of pieces of the respiration information, the biological condition determining unit 32 may either compare each of them with the referential signal to see whether or not each of them matches the referential signal, or determine the respiratory condition of the subject S on the basis of whether or not all of them match the referential signal.

Further, in the embodiment described above, the load signals are sent to the body posture identifying unit 33 via the biological information extracting unit 31. However, the load signals may be sent directly from the A/D converting unit 2 to the body posture identifying unit 33.

Further, in the embodiment described above, the biological condition determining unit 32 determines whether or not the respiration information matches or resembles the snore information, determines whether or not the respiration information matches or resembles the apnea information and, if the respiration information neither matches nor resembles any of the snore information and the apnea information, determines that the subject S is in the ordinary respiratory state. However, without being limited to that, the biological condition determining unit 32 may, for example, determine whether or not the respiration information matches or resembles the ordinary respiration information, determines whether or not the respiration information matches or resembles the snore information and, if the respiration information neither matches nor resembles any of the ordinary respiration information and the snore information, determines that the subject S is in the apneic state. Further, the biological condition determining unit 32 may determine whether or not the respiration information matches or resembles the apnea information. In addition, the biological condition determining unit 32 may perform the step of determining the respiratory condition of the subject S by any preferred procedure including a comparison of the respiration information with at least one of the ordinary respiration information, the snore information, the apnea information, and the like.

Further, in the embodiment described above, in order to further increase the accuracy for the body posture identifying unit 33 to identify the body posture of the subject S, the following methods may be used. A first example is to prepare a corresponding relation between the body postures of the subject S and the detected values of the load detectors 11, 12, 13, 14 stored in the body posture identifying unit 33 as a plurality of variations of corresponding relations. Here, the a plurality of variations of corresponding relations are classified by the body height, body weight, muscle mass, body fat percentage and the like of each of a plurality of virtual subjects Si (i=1, 2, . . . , n). Then, when the biological condition determining apparatus 100 is in use, the body height, body weight, muscle mass, body fat percentage and the like of the actual subject S is inputted via the input unit 7 before identifying the body posture of an actual subject S. By virtue of this, the body posture identifying unit 33 uses a set of the corresponding relations satisfying the above conditions to identify the body posture.

A second example is as follows. Firstly, the subject S on the bed performs a series of body posture changes according to a specific protocol, and then, based on that, corresponding relations between the body postures and the detected load values unique to the subject S are created.

A third example is to use the biological condition determining apparatus 100 to detect the load signals over one night while recording the sleeping form of the subject S with a video camera or the like, and to compare the obtained load signals with the recorded image to create the corresponding relations between the body postures and the detected load values.

Further, the biological condition determining apparatus 100 of the embodiment described above may not have the body posture identifying unit 33 and/or the associating unit 34.

Note that in the biological condition determining apparatus 100 of the embodiment described above, the display unit 5 may be a unit which displays the respiratory condition only. Further, the display unit is not limited to a unit which displays the information on the monitor so that the user can make the visual recognition. For example, the display unit 5 may be a printer which prints and outputs the respiratory condition of the subject S. Alternatively, the display unit 5 may be a unit which performs the display by using any simple visual expression, for example, such that a blue lamp is turned ON if the subject is in the ordinary respiratory state, a yellow lamp is turned ON if the subject is in the snoring state, and/or a red lamp is turned ON if the subject is in the apneic state. Further alternatively, the display unit 5 may be a unit which reports the respiratory condition of the subject S to the user by means of any sound or voice.

Further, the biological condition determining apparatus 100 of the embodiment described above may not have the display unit 5. In this case, the biological condition determining apparatus 100 may include a signal output unit (not depicted) for outputting the biological condition of the subject S obtained with the control unit 3 to a data logger or the like. Via the signal output unit, the biological condition of the subject S obtained with the control unit 3 is sent to and stored in the data logger or the like in the form of image signal, text information, binary information, and the like. In this specification, the display unit and the signal output unit are collectively referred to as the "output unit".

Note that the notifying unit 6 of the embodiment described above performs the notification auditorily. However, the notifying unit 6 may be constructed to perform the notification visually by means of, for example, the flashing or flickering of light. Alternatively, the notifying unit 6 may be constructed to perform the notification by means of the vibration. Further, it is also allowable that the biological condition determining apparatus 100 of the embodiment described above does not have the notifying unit 6.

Note that the components of the biological condition determining apparatus 100 of the embodiment described above, which are connected to one another by means of the wirings, may be connected to one another in a wireless manner.

The present invention is not limited to the embodiments described above provided that the feature of the present invention is maintained. Other embodiments, which are conceivable within the scope of the technical concept of the present invention, are also included in the scope of the present invention.

The biological condition determining apparatus according to the above embodiments may further include a body posture identifying unit which obtains a body posture of the subject based on outputs of the load detectors, wherein the output unit may output the body posture of the subject obtained by the body posture identifying unit.

The biological condition determining apparatus according to the above embodiments may further include an associating unit which associates the biological condition of the subject determined by the determining unit with the body posture of the subject obtained by the body posture identifying unit.

In the biological condition determining apparatus according to the above embodiments, the output unit may output the obtained body posture of the subject by using an image imitating a human body shape.

In the biological condition determining apparatus according to the above embodiments, the determining unit may determine whether a respiratory condition (that is a kind of the biological condition) of the subject is an ordinary respiratory state, a snoring state, or an apneic state.

The biological condition determining apparatus according to the above embodiments may further include: a storage unit which stores the referential information; an information collecting unit which associates the biological information used in the determining unit to determine the biological condition of the subject with a determination result of the determining unit so as to create an update information; and an information editing unit which modifies the referential information based on the update information.

The biological condition determining apparatus according to the above embodiments may further include a notifying unit which performs a notification based on a determination result of the determining unit.

The biological condition determining method according to the above embodiments may further include obtaining a body posture of the subject by using a body posture identifying unit based on outputs of the load detectors.

The biological condition determining method according to the above embodiments may further include associating the determined biological condition of the subject with the obtained body posture of the subject, by using an associating unit.

According to the biological condition determining apparatus and the biological condition determining method of the above embodiments, it is possible to determine the biological condition of a subject on a bed in a detailed manner without using a sensor mat and/or other expensive and complex devices.

The biological condition determining apparatus of the embodiment described above extracts the biological information which is included (contained) in the output from the load detector and denotes the biological condition of the subject, and compares the same with the referential information prepared beforehand, so as to determine the biological condition of the subject. In this manner, by using the referential information, it is possible to determine the biological condition of each and every subject in a detailed and correct manner.

Because biological condition determining apparatus of the embodiment described above has the body posture identifying unit, it is possible to satisfactorily identify various body postures of the subject, and present the same to the user.

Because the biological condition determining apparatus of the embodiment described above has the associating unit, it is possible to satisfactorily present the user with the relationship between the biological condition and the body posture of the subject.

Because the biological condition determining apparatus of the embodiment described above performs the output by using the image imitating a human body shape, it is possible for the user to intuitively and easily grasp the body posture of the subject.

According to the biological condition determining apparatus of the embodiment described above, it is possible to satisfactorily diagnose whether or not there is a pathological condition such as the sleep apnea syndrome and other diseases and, if any, treat the same, by determining whether the subject is in the ordinary respiratory state, the snoring state, or the apneic state.

Because the biological condition determining apparatus of the embodiment described above has the information collecting unit and the information editing unit, it is possible to improve or enhance the referential information used by the biological condition determining apparatus, while using the biological condition determining apparatus for the subject.

Because the biological condition determining apparatus of the embodiment described above has the notifying unit, it is possible for the user to instantly and reliably know that the subject has come into a predetermined state.

In the biological condition determining method of the embodiment described above, it is configured to extract the biological information which is included (contained) in the output from the load detector and denotes the biological condition of the subject, and compare the same with the referential information prepared beforehand, so as to determine the biological condition of the subject. Therefore, by using the referential information, it is possible to determine the biological condition of each and every subject in a detailed and correct manner.

In the biological condition determining method of the embodiment described above, because the body posture identifying unit is used to identify the body posture, it is possible to satisfactorily identify various body postures of the subject, and present the same to the user.

In the biological condition determining method of the embodiment described above, because the associating unit is used, it is possible to satisfactorily present the user with the relationship between the biological condition and the body posture of the subject.

According to the biological condition determining apparatus of one aspect of the present disclosure, it is possible to quantitatively measure the magnitude of the respiratory rate and/or the respiratory volume (ventilatory volume) from a change in the load distribution, and to successively monitor the respiratory condition of a hospitalized patient without incursion and contact. Further, it is possible to automatically input the respiratory condition into the nursing record (vital record) and display the same, and it is possible to automatically transmit information on the deterioration of the respiratory condition to the nurse. Therefore, it is possible to decrease the number of times of the checking for the patient at night by the nurse, it is possible to decrease the amount of work of the nurse, and it is possible to improve the quality of the sleep of the patient.

The invention claimed is:

1. A biological condition determining apparatus for determining a biological condition of a subject on a bed, the apparatus comprising:
   a plurality of load detectors which are configured to be placed in the bed or under legs of the bed and which detect a load of the subject; and
   a controller configured to:
   extract a plurality of pieces of respiration information from outputs of the plurality of load detectors, respectively;
   determine a respiratory condition of the subject by comparing at least one of the extracted plurality of pieces of respiration information with a referential information prepared beforehand; and
   output the determined respiratory condition of the subject,
   wherein the plurality of pieces of respiration information is a plurality of detected waveforms showing temporal variations, based on a respiration of the subject, of the outputs of the plurality of load detectors, respectively, wherein the referential information is a plurality of types of referential waveforms denoting a plurality of types of respiratory conditions of the subject, respectively, and wherein the comparison is between a waveform, among the plurality of detected waveforms, having a largest amplitude and the plurality of types of referential waveforms stored beforehand, and wherein when the waveform having the largest amplitude matches or resembles one of the plurality of types of referential waveforms, the controller is configured to determine that the respiratory condition of the subject is one of the plurality of types of respiratory conditions denoted by the one of the plurality of types of referential waveforms that matches or resembles the waveform having the largest amplitude.

2. The biological condition determining apparatus according to claim 1, wherein the controller is further configured to obtain a body posture of the subject based on outputs of the load detectors, and to output the obtained body posture of the subject.

3. The biological condition determining apparatus according to claim 2, wherein the controller is further configured to associate the determined respiratory condition of the subject with the obtained body posture of the subject.

4. The biological condition determining apparatus according to claim 2, wherein the controller is configured to output the obtained body posture of the subject by using an image imitating a human body shape.

5. The biological condition determining apparatus according to claim 1, wherein the controller is configured to determine whether the respiratory condition of the subject is an ordinary respiratory state, a snoring state, or an apneic state.

6. The biological condition determining apparatus according to claim 1, further comprising:
memory configured to store the referential information, wherein the controller is further configured to:
associate the respiration information with the determined respiratory condition so as to create an update information; and
modify the referential information based on the update information.

7. The biological condition determining apparatus according to claim 1, wherein the controller is further configured to cause the biological condition determining apparatus to perform a notification based on a determination result of the determining of the respiratory condition of the subject.

8. A method for determining a biological condition of a subject on a bed, the method comprising:
detecting a load of the subject by using a plurality of load detectors placed in the bed or under legs of the bed;
extracting a plurality of pieces of respiration information from outputs of the plurality of load detectors, respectively; and
determining a respiratory condition of the subject by comparing at least one of the extracted plurality of pieces of respiration information with a referential information prepared beforehand, wherein the plurality of pieces of respiration information is a plurality of detected waveforms showing temporal variations, based on a respiration of the subject, of the outputs of the plurality of load detectors, respectively, wherein the referential information is a plurality of types of referential waveforms denoting a plurality of types of respiratory conditions of the subject, respectively, and wherein the comparison is between a waveform, among the plurality of detected waveforms, having a largest amplitude and the plurality of types of referential waveforms stored beforehand, and wherein when the waveform having the largest amplitude matches or resembles one of the plurality of types of referential waveforms, the method further comprises determining that the respiratory condition of the subject is one of the plurality of types of respiratory conditions denoted by the one of the plurality of types of referential waveforms that matches or resembles the waveform having the largest amplitude.

9. The method according to claim 8, further comprising obtaining a body posture of the subject based on outputs of the load detectors.

10. The method according to claim 9, further comprising associating the determined respiratory condition of the subject with the obtained body posture of the subject.

11. The biological condition determining apparatus according to claim 1, wherein the plurality of types of referential waveforms stored beforehand includes a first referential waveform denoting that the respiratory condition of the subject is an ordinary respiratory state, a second referential waveform denoting that the respiratory condition of the subject is a snoring state, and a third referential waveform denoting that the respiratory condition of the subject is an apneic state.

12. The method according to claim 8, wherein the plurality of types of referential waveforms stored beforehand includes a first referential waveform denoting that the respiratory condition of the subject is an ordinary respiratory state, a second referential waveform denoting that the respiratory condition of the subject is a snoring state, and a third referential waveform denoting that the respiratory condition of the subject is an apneic state.

* * * * *